US00PP13109P2

(12) United States Plant Patent
Olesen et al.

(10) Patent No.: US PP13,109 P2
(45) Date of Patent: Oct. 22, 2002

(54) ROSE PLANT NAMED 'POULRA003'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/780,138

(22) Filed: Feb. 8, 2001

(51) Int. Cl.[7] ..... A01H 5/00
(52) U.S. Cl. ..... Plt./122
(58) Field of Search ..... Plt./122

(56) References Cited

PUBLICATIONS

UPOV–ROM GTITM Computer Database, 2001/04, GTI Jouve Retrieval Software, citation for 'POULra003'.*

* cited by examiner

*Primary Examiner*—Bruce R. Campell
*Assistant Examiner*—Susan B. McCormick

(57) ABSTRACT

A new miniature rose plant which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

BOTANICAL CLASSIFICATION

*Rosa hybrida.*

VARIETY DENOMINATION

'POULra003'.

SUMMARY OF THE INVENTION

The present discovery constitutes a new and distinct variety of a miniature pot rose plant which was discovered in a cultivated area. The mutation resulted from 'POULrac', a miniature pot rose hybridized by the same inventors. 'POULrac' is described and illustrated in U.S. Plant Pat. No. 11,543, and issued on Oct. 3, 2000. The new rose variety resulted from a naturally occurring mutation of unknown causation on a branch of 'POULrac'. 'POULra003' is distinguished from 'POULrac' by the lighter red flowers compared to the darker red flowers of 'POULrac'. The rose plant of the present discovery has a unique combination of characteristics which are outstanding in the new variety and which distinguish it from the original rose 'POULrac' as well as all other varieties which we are aware of. For example, the new variety has:

1. Uniform and abundant red flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULra003' from all other varieties of which we are aware.

The resulting mutation was selected and evaluations were conducted on the resulting rose plants in a controlled environment.

Asexual reproduction of 'POULra003' by cuttings and traditional budding was first done by L. Pernille and Mogens N. Olesen in their nursery in Fredensborg, Denmark in June, 1999. This initial and other subsequent propagations conducted in controlled environments have demonstrated that the characteristics of 'POULra003' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra003'. Specifically illustrated in SHEET 1:

1. Stem showing branching and the attachment of leaves, buds, and peduncles:
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

The following is a description of 'POULra003', as observed in its growth in greenhouses in Burlington, Canada, on plants aged sixteen weeks. Root development for the observed plant typically takes 8 to 10 weeks. Color references are made using The Royal Horticultural Society (London, England) Colour Chart, 1995, except where common terms of color are used.

For a comparison, several physical characteristics of the rose variety 'POULrac', a rose variety from the same inventors described and illustrated in U.S. Plant Pat. No. 11,543 and issued on Oct. 3, 2000 are compared to 'POULra003' in Chart 1.

CHART 1

| | 'POULra003' | 'POULrac' |
|---|---|---|
| Bud color at ¼ opening | Red Group 51A | Red Group 53A to Red-Purple Group 60B |
| Inner side of petal surface, open | Red Group 53C | Between Red Group 46A and Red-Purple Group |

CHART 1-continued

| | 'POULra003' | 'POULrac' |
|---|---|---|
| bloom | | 60B |
| Outer side of petal surface, open bloom | Red Group 53C | Red Group 46A |

Classification:

(*Genus, Species, Cultivar*).—*Rosa Hybrida* POULra003.

*Commercial.*—Miniature.

FLOWER AND FLOWER BUD

Blooming habit: Continuous.

Flower bud:

*Size.*—Upon opening, 18–20 mm in length from base of receptacle to end of bud.

*Bud form.*—Short and globular.

*Bud color.*—As sepals unfold, Red Group 51A. Red Group 51A at ¼ opening.

*Sepals.*—Yellow-Green Group 146B. Weak foliaceous appendages on three of the five sepals. Surfaces of sepals moderately pubescent. Stipitate glands present along margins. Sepals are 18–22 mm long and 5–7 mm wide.

*Receptacle.*—Surface: Smooth. Shape: Urn-shaped. Size: Small. 4–5 mm (l)×4–5 mm (w). Color: Yellow-Green Group 144B.

*Peduncle.*—Surface: Generally smooth with a limited number of stipitate glands. Length: 35–50 mm average length. Color: Yellow-Green Group 144A. Strength: Erect.

*Borne.*—Multiple buds, 2–5 buds per stem.

*Anthocyanin.*—None observed.

Flower bloom:

*Fragrance.*—None.

*Duration.*—As a pot plant, flowers last from 16 to 18 days. As a cut flower 5 to 7 days. The blooms have a duration on the plant of approximately 10 to 12 days.

*Size.*—Medium for an 8–11 cm pot rose. Average flower diameter is 30–35 mm when open.

*Form.*—Shape of flower when viewed from the side: Upon opening, upper part: Flat. Upon opening, lower part: Flattened convex. Open flower, upper part: Flat. Open flower, lower part: Flattened convex.

*Petalage.*—Very double: 40–48 petals under normal conditions with 0–5 petaloids.

Color:

*Upon opening, petals.*—Outermost petals: Outer Side: Red Group 51A. Inner Side: Red Group 50A–51A. Innermost petals: Outer Side: Red Group 51A. Inner Side: Red Group 50A.

*Upon opening, basal petal spots.*—Outermost petals: Outer Side: Green-White Group 157A. Inner Side: Green-White Group 157C. Innermost petals: Outer Side: Yellow-Green Group 154C. Inner Side: Green-Yellow Group 1D.

*After opening, petals.*—Outermost petals: Outer Side: Red Group 53C. Inner Side: Red Group 53C. Innermost petals: Outer Side: Red Group 54A. Inner Side: Red Group 54A.

*After opening, basal petal spots.*—Outermost petals: Outer Side: Green-Yellow Group 1D. Inner Side: Green-Yellow Group 1C–D. Innermost petals: Outer Side: Yellow-Green Group 145D. Inner Side: Yellow-Green Group 145C.

General tonality: On open flower Red Group 52A. Flower tone is constant as flowers age with no perceptible color change.

Petals:

*Petal reflex.*—Somewhat.

*Petal edge.*—Slightly ruffled.

*Shape.*—Deltoid; base is flat at union with peduncle.

*Petaloids.*—Present; Quantity: 0–5.

*Thickness.*—Thin.

*Arrangement.*—Imbricated.

*Size.*—Petals are 15 mm long and 10–12 mm wide.

Reproductive organs:

*Pollen.*—Color: Greyed-Orange Group 163C. Quantity: Average.

*Anthers.*—Size: Small. Color: Greyed-Yellow Group 161C. Quantity: Very abundant.

*Filaments.*—Color: Yellow-Orange Group 17C.

*Stigmas.*—Slightly superior in location to anthers. Color: Yellow-Orange Group 16B.

*Styles.*—Color: Green-White Group 157C.

*Hip formation.*—Not observed.

PLANT

Plant growth: Vigorous and compact. When grown as an 8–11 cm pot plant, the average height of the plant is 16–20 cm and the average width is 20–23 cm.

Stems:

*Color.*—Young wood: Yellow-Green Group 144A. Older wood: Yellow-Green Group 144A.

*Prickles.*—Incidence: Moderate. Size: Average length: 2–4 mm. Color: Greyed-Yellow Group 160A. Shape: Linear to slightly concave.

*Surface.*—Young wood: Smooth. Older wood: Smooth.

*Length.*—Stem length is typically 20 to 25 cm.

*Diameter.*—Stem diameter is typically 4 to 6 mm.

Plant foliage: Typical number of leaflets on normal leaves in middle of the stem: 5–7 leaflets.

*Leaf size.*—Small. 50–60 mm (l)×30–35 mm (w).

*Abundance.*—Average.

*Color.*—Mature Foliage: Upper Leaf Surface: Yellow-Green Group 147A. Lower Leaf Surface: Yellow-Green Group 147B. Juvenile foliage: Upper Leaf Surface: Yellow Green Group 146A. Lower Leaf Surface Yellow-Green 146C–D. Anthocyanin intonation: None.

Plant leaves and leaflets:

*Stipules.*—Size: 6–7 mm (l)×3–4 mm (w). Color: Yellow-Green Group 144B. Stipitate glands: Along margins. Anthocyanin: None.

*Petiole.*—Length: 12–16 mm. Color: Yellow-Green Group 144C. Underneath: Smooth. Margins: Stipitate glands present. Anthocyanin: Stipitate glands along margins have intonations of Greyed-Red Group 181A.

*Rachis.*—Color: Yellow-Green Group 146B. Underneath: Generally smooth with a few small prickles. Margins: Stipitate glands present. Anthocyanin: Stipitate glands and margins have intonations of Greyed-Red Group 181A.

*Leaflet.*—Edge: Finely serrated. Shape: Ovate. Other: Matte finish and thin.

Disease resistance: Above average resistance to mildew, black spot, and Botrytis under normal growing conditions in Burlington, Canada.

Cold hardiness: The variety 'POULra003' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant red flowers, vigorous growth, compact habit, suitability for production from softwood cuttings in pots, and durable flowers and foliage which make the variety suitable for distribution in the floral industry.

* * * * *

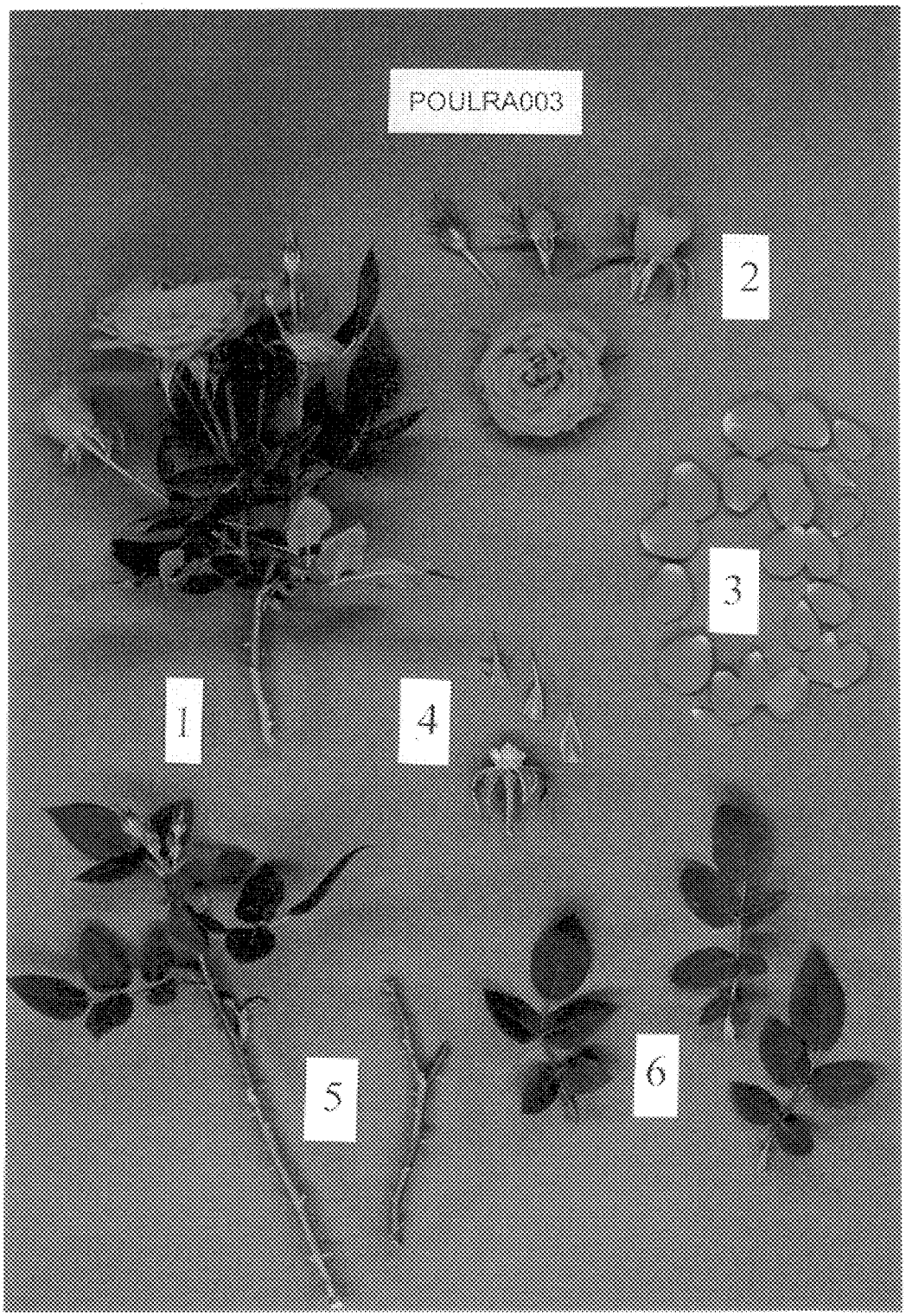
POULRA003
1
2
3
4
5
6